United States Patent
Meyer

(10) Patent No.: US 11,739,207 B2
(45) Date of Patent: Aug. 29, 2023

(54) COMPOSITION FOR INTERFACE DRESSING

(71) Applicant: Urgo Recherche Innovation et Developpement, Chenove (FR)

(72) Inventor: Nadège Meyer, Tart le Haut (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 84 days.

(21) Appl. No.: 16/629,141

(22) PCT Filed: Jul. 12, 2018

(86) PCT No.: PCT/FR2018/051759
§ 371 (c)(1),
(2) Date: Jan. 7, 2020

(87) PCT Pub. No.: WO2019/012230
PCT Pub. Date: Jan. 17, 2019

(65) Prior Publication Data
US 2020/0190310 A1    Jun. 18, 2020

(30) Foreign Application Priority Data

Jul. 12, 2017 (FR) ........................... 1756589

(51) Int. Cl.
*C08L 53/02* (2006.01)
*A61L 15/24* (2006.01)
*A61L 15/44* (2006.01)

(52) U.S. Cl.
CPC ............. *C08L 53/02* (2013.01); *A61L 15/24* (2013.01); *A61L 15/44* (2013.01); *A61L 2300/412* (2013.01); *C08L 2205/02* (2013.01); *C08L 2205/03* (2013.01)

(58) Field of Classification Search
CPC ...... C08L 53/02; C08L 2205/03; A61L 15/24; A61L 2300/412
USPC .................................................... 514/772.1
See application file for complete search history.

(56) References Cited

U.S. PATENT DOCUMENTS

| | | | |
|---|---|---|---|
| 4,892,903 A * | 1/1990 | Himes | C08J 5/18 524/487 |
| 7,093,599 B2 * | 8/2006 | Chen | C08L 53/025 128/112.1 |
| 8,967,161 B2 * | 3/2015 | Wong | A61Q 11/00 132/321 |
| 2002/0128345 A1 * | 9/2002 | Paul | A61K 9/7076 523/112 |
| 2010/0285129 A1 | 11/2010 | Laurensou | |
| 2015/0174285 A1 | 6/2015 | Auguste et al. | |

FOREIGN PATENT DOCUMENTS

| | | | |
|---|---|---|---|
| FR | 3030225 | * | 6/2016 |
| FR | 3233003 B1 | * | 9/2018 |
| WO | 2016/097653 A1 | | 6/2016 |

OTHER PUBLICATIONS

Product brochure of Poly(4-methylstyrene) with an average molecular weight of 72,000, # 182273 by Sigma-Aldrich (7 pages, Downloaded from Google Search on Jun. 7, 2022).*
3-page Technical data sheet for KRISTALEX 3085 by EASTMAN Chemical Company, Downdloaded on Sep. 27, 2022.*
11-page Product brochure for SEPTON by Kuraray Co., Downloaded on Sep. 27, 2022.*
Brochure for Johnson & Johnson ADAPTIC Non-Adhering Dressing, J&J 2012, 2013, 2014, 5 pages.*
International Search Report issued in corresponding International Patent Application No. PCT/FR2018/051759 dated Oct. 2018.

* cited by examiner

*Primary Examiner* — Tae H Yoon
(74) *Attorney, Agent, or Firm* — Morgan, Lewis & Bockius LLP

(57) ABSTRACT

The present invention relates to a novel composition based on ABA triblock copolymers comprising two styrene thermoplastic end blocks A and a central elastomeric block B which is a saturated olefin, comprising at least one resin chosen from the aromatic resins, that can be used in particular for producing an interface dressing with reinforcement, with a support or which is self-supported, preferably self-supported. The present invention relates to a self-supported interface dressing which can be easily handled since it has good tear strength.

11 Claims, No Drawings

COMPOSITION FOR INTERFACE DRESSING

CROSS-REFERENCE TO RELATED APPLICATIONS

This application is a 371 National Stage Application, which claims the benefit of International Application No. PCT/FR2018/051759, filed on Jul. 12, 2018, which claims priority to French Patent Application No. 1756589, filed on Jul. 12, 2017, the contents of which are hereby incorporated by references in their entirety.

SUMMARY

The present invention relates to a novel composition based on ABA triblock copolymers comprising two styrene thermoplastic end blocks A and a central elastomeric block B which is a saturated olefin, and at least one resin chosen from the aromatic resins, that can be used in particular for producing an interface dressing comprising a framework or a substrate, or a self-supporting interface dressing, preferably self-supporting.

The present invention also relates to a self-supporting interface dressing which is easier to handle because it has a good tear strength.

PRIOR ART

The treatment of wounds by dressings, termed "interface dressings", intended to be placed in contact with the wound, providing an interface between the wound and an absorbent compress that is placed on the dressing in order to absorb the exudates, has long been known.

The URGOTUL® dressing marketed since 2000 by Laboratoires URGO is an illustrative example of an interface dressing. The URGOTUL® product is composed of a framework made of an open mesh fabric, the threads of which are coated with a cohesive gel, in such a way as to leave the meshes substantially unblocked. This gel is formed of a composition composed of a strongly plasticised elastomeric matrix based on ABA (styrene-saturated olefin-styrene) triblock copolymers and containing, in dispersion, a small quantity of hydrophilic particles of a hydrocolloid. This dressing and its composition are described in example 1 of patent application WO 00/16725. The qualitative and quantitative composition of the elastomeric matrix of this dressing gives it remarkable properties in terms of the promotion of the healing process and, in particular, the proliferation of fibroblasts.

However, in cases where it is desired to apply it on wounds that are difficult to cover, for example because of their location, URGOTUL® has the disadvantage of lacking conformability, because of the rigidity of its framework.

In order to solve this problem, self-supporting interface dressings (without framework) have been described in patent application FR 2 936 158. The products described in this application have both a good elasticity and a sufficient cohesion for being handled. However, the self-supporting interface dressings described in this document use constituents different from the ABA triblock polymers employed in the URGOTUL® dressing, so that the healing properties and proliferation of fibroblasts is not retained.

Moreover, in terms of economic profitability, it would be desirable for the applicant to be able to produce a self-supporting interface dressing from compounds of the same type as, or even identical to, those used for the production of the URGOTUL® dressing and its variations, which the applicant already produces.

In addition to the economic aspect, this would also present a non-negligible advantage in the case where it was desired to incorporate active compounds in the composition of the self-supporting interface dressing, in other words compounds which have an action on the healing process or the treatment of the wound, such as for example antibacterials, such as silver salts, or inhibitors of MMP (matrix metalloproteinases) such as potassium sucrose octasulfate. Indeed, the incorporation of active ingredients in this type of composition is always delicate and complex, each compound of the composition can interact with the others, modifying the rheological and physicochemical properties of the composition, or even affecting the stability or solubility of the active ingredient.

By using compounds of the same type as those already used for the production of the URGOTUL® dressing, the chances of developing novel compositions having the desired advantages are therefore optimised.

Finally, the use of compounds of the same type as, or even identical to, those used for producing the URGOTUL® dressing could make it possible to retain the remarkable properties of the URGOTUL® product on the proliferation of fibroblasts and on the healing process.

It would therefore be desirable to have a composition for an interface dressing composed of compounds of the same type as, or identical to, those used in the URGOTUL® product, making it possible to prepare interface dressings that have good conformability and a good tear strength, even without framework.

SUMMARY OF THE INVENTION

Thus, the present invention has developed a specific composition made from ABA triblock polymers, comprising two thermoplastic styrene terminal blocks A and a central elastomeric block B which is a saturated olefin, allowing the preparation of an elastomeric matrix that can be used in a dressing, which is preferably self-supporting, said matrix having a very good tear strength.

More specifically, it has been discovered, and this constitutes the basis of the present invention, that compositions comprising at least two specific triblock copolymers (elastomers) of the type styrene-saturated olefin-styrene, and at least one aromatic resin present within the composition in a predetermined quantity by weight, make it possible to produce dressings having improved mechanical properties. Indeed, the dressings obtained with the elastomeric matrices of the invention are easy to handle, and the risk of tearing at the time of application or at the time of removal of the dressing by care personnel is reduced. Once applied, the dressings obtained with these elastomeric matrices have an improved conformability and the contact with the wound bed is therefore promoted. Due to its improved elasticity, the dressing is better able to follow the movements of the patient, and the reinforcement of its mechanical properties prevents the dressing disintegrating in the wound, even after contact with the exudates of the wound over a prolonged period.

The addition of specific resins makes it possible to reduce the viscosity of the elastomeric mixture and to mechanically strengthen the elastomeric matrix. This is particularly advantageous in the method for producing the elastomeric matrix. The reduced viscosity allows the composition to be coated more easily onto a framework. In the case of a self-supporting dressing, the improvement in cohesion of the elastomeric matrix makes possible a better moulding and demoulding thereof. In addition, due to the specific resins used, the production temperature of the composition can be reduced by approximately 10° C., which makes it possible to introduce components into the mixture which are sensitive to thermal treatments, such as active ingredients for example. According to a preferred embodiment, the dressing according to the invention does not adhere to latex surgical gloves.

Elastomer based compositions for releasing active agents have already been proposed, for example, in document US2002/0128345. This document describes pressure-sensitive adhesive compositions, using high-viscosity triblock copolymers in combination with tackifying resins giving the composition sticking properties. In particular, the compositions preferably comprise a diblock copolymer of particularly high viscosity. The matrices obtained by means of the compositions described in US2002/0128345 thus have particularly high adherence properties to the skin. Such compositions are not however suitable for use in self-supporting interface dressings, which need to be placed in contact with a wound to which it is imperative that it does not adhere, in order to allow an atraumatic removal of the dressing. Such interface dressings are generally used in association with a retaining device, such as a tape (also called a secondary dressing). In addition, adhesive compositions according to US2002/0128345 do not have the desired ease of handling for such dressings. Finally, the stickiness conferred on such compositions inherently alters the cohesion of the matrices (in the context of a self-supporting interface dressing, cohesion means the mechanical behaviour) obtained from these compositions. Indeed, the compositions described in this document are particularly viscous and trap air bubbles in their structure during the production process. Hence, these bubbles are incorporated in the structure of the matrices obtained from such compositions, weakening their structure.

Thus, according to a first aspect, the present invention relates to a composition, particularly useful for the production of dressings, comprising:

5 to 20% of a mixture of two triblock copolymers of the type styrene-saturated olefin-styrene, a first which has a viscosity between 0.01 and 1 Pa·s as measured in a 5% (mass/mass) solution in toluene and a second which has a viscosity between 0.01 and 0.5 Pa·s as measured in a 15% (mass/mass) solution in toluene, 50 to 80% by weight of at least one plasticiser, 5 to 20% of at least one alpha-methylstyrene resin, having a softening point in the range between 80 and 125° C., preferably between 90 and 110° C., it being understood that:

when the content of triblock copolymers is between 5 and 10% by weight, the content of resin is between 15 and 20% by weight, with respect to the total weight of the composition, and when the content of triblock copolymers is greater than 10% by weight, the content of resin is between 5 and 20% by weight, with respect to the total weight of the composition, and the percentages being with respect to the total weight of the composition.

According to a second aspect, the present invention relates to an elastomeric matrix obtained from such a composition and an interface dressing, with substrate or self-supported, comprising said elastomeric matrix.

DETAILED DESCRIPTION

Elastomer

The composition according to the invention comprises at least one mixture of two ABA triblock copolymers.

In particular this mixture of two copolymers, comprises at least one copolymer which has a viscosity between 0.01 and 1 Pa·s measured in a 5% mass/mass solution in toluene and at least one copolymer having a viscosity between 0.01 and 0.5 Pa·s measured in a 15% (mass/mass) solution in toluene.

The block copolymers used in the context of the invention are ABA triblock copolymers comprising two thermoplastic styrene terminal blocks A and a central elastomeric block B which is a saturated olefin. The B blocks of saturated olefins are, for example, ethylene-butylene, ethylene-propylene or ethylene-ethylene-propylene blocks.

For the sake of simplicity, in the present description, the polymer blocks constituting the above-mentioned copolymers are designated by the nature of their recurrent units. Thus, the expression "block" or "styrene block A" designates a poly(styrene) block and the expression "block" or "saturated olefin block" designates a poly(saturated olefin) block.

Triblock copolymers with a saturated central block are well known to a person skilled in the art and are marketed, for example:

by KRATON under the name KRATON® G, and, in particular, the grades KRATON® G1651, KRATON® G1654, KRATON® G 1657, KRATON® G1652 or KRATON® G1650, and by KURARAY under the name SEPTON® and, in particular, the grades 8006 or 8004 for poly(styrene-ethylene-butylene-styrene) block copolymers (abbreviated as SEBS);

by KURARAY under the name SEPTON® for poly(styrene-ethylene-propylene-styrene) block copolymers (abbreviated as SEPS) and in particular the grades 2005, 2006 or 2063 and for poly(styrene-ethylene-ethylene-propylene-styrene) block copolymers (abbreviated as SEEPS) and in particular the grades 4033, 4044, 4055, 4077 or 4099.

In the framework of the present invention, SEBS, SEPS or SEEPS triblock copolymers having a styrene content between 25 and 45% by weight with respect to the weight of said SEBS, SEPS or SEEPS copolymer are preferred.

Copolymers having a viscosity between 0.01 and 1 Pa·s, measured in a 5% (mass/mass) solution in toluene, include the copolymers marketed by KRATON under the grades KRATON® G 1651 and KRATON® G 1654 and copolymers marketed by KURARAY under the grades SEPTON® 2005, 2006, 8006, 4055, 4077, 4044 or 4099.

Copolymers having a viscosity between 0.01 and 0.5 Pa·s, measured in a 15% (mass/mass) solution in toluene, include the copolymers marketed by KRATON under the grades KRATON® G 1650, KRATON® G 1657 and KRATON® G 1652 and copolymers marketed by KURARAY under the grades SEPTON® 2063 or 4033.

These viscosities are measured at 30° C. using a Brookfield model LVI viscometer in a 5% or 15% (mass/mass) solution in toluene, depending on the molecular weight of the copolymer. In particular, viscosities are measured according to standard ISO2555.

In general, the quantity of copolymers in the final composition can be between 5 and 20% by weight, preferably between 7 and 15% by weight, with respect to the total weight of the composition.

In the context of the present invention, it is particularly preferred to use two SEBS block copolymers, and in particular the combination of the copolymers KRATON® G 1654 and KRATON® G 1650 wherein KRATON® G 1654 is present in a quantity of 5 to 10% by weight with respect to the total weight of the composition, and KRATON® G 1650 is present in a quantity of 2 to 5% by weight, with respect to the total weight of the composition.

Preferably, this mixture of two copolymers therefore comprises at least 5 to 10% by weight of one copolymer which has a viscosity between 0.01 and 1 Pa·s measured in a 5% mass/mass solution in toluene and at least 2 to 5% of a copolymer having a viscosity between 0.01 and 0.5 Pa·s measured in a 15% (mass/mass) solution in toluene, with respect to the total weight of the composition.

In particular, the composition according to the invention comprises no diblock polymer, in particular does not comprise any styrene hydrogenated isoprene diblock polymer.

The Resins

The resins used in the composition according to the invention are aromatic hydrocarbon resins, in other words made uniquely from aromatic monomers. They differ from aliphatic resins, made uniquely from aliphatic monomers, or aliphatic/aromatic resins, made from aliphatic and aromatic monomers. Without wishing to be bound by any particular theory, it appears that these resins have a good solubility in the block A of the ABA copolymers and strengthen this styrene block, which improves the cohesion of the final elastomeric matrix obtained.

The aromatic monomer is, in particular, alpha-methylstyrene. Thus, according to a particularly preferred embodiment, the aromatic hydrocarbon resin is chosen from the homopolymer and copolymer resins of alpha-methyl-styrene.

Among the aromatic resins tested, a certain number were not entirely satisfactory. Indeed, some grades of resin, due to their high softening point, needed to be heated to high temperatures (greater than 140° C.) in order to produce the composition of the invention. When working at such temperatures, there is a risk of the plasticiser evaporating. When hydrocolloids (such as carboxymethyl cellulose) or active ingredients are added to the composition, these may degrade.

Thus, the resins used in the compositions according to the invention are alpha-methylstyrene resins having a softening point in the range between 80 and 125° C., preferably between 90 and 110° C.

These resins give the best results in terms of production process, breaking force and elongation at break. The addition of such resins reduces the viscosity of the mixture and mechanically strengthens the composition, thus facilitating its transformation into a tear resistant polymer matrix.

The softening point is measured according to standard ISO 4625 ("Ring and Ball" method).

Preferably, the resin according to the invention is an alpha-methylstyrene resin having a softening point in the range between 95 and 105° C. or between 115 and 125° C. or a poly(styrene-co-alpha-methylstyrene) resin having a softening point between 95° C. and 115° C.

The preferred resins above are well known to a person skilled in the art and are commercially available, sold for example under the following tradenames:

Sylvares SA 100 and Sylvares SA 120 from Arizona Chemical: alpha-methylstyrene resins having a softening point in the range between 95 and 105° C. or between 115 and 125° C. respectively, Cleartack W90 or Norsolene W90 resin from Cray Valley: poly(styrene-co-alpha-methylstyrene) resin having a softening point between 85 and 95° C., the resins Kristalex 3100LV, Kristalex F100, Kristalex 3105SD and Kristalex F115 from Eastman: poly(styrene-co-alpha-methylstyrene) resins having a softening point of 100° C., or between 96 and 104° C. or of 105° C., or between 114 and 120° C. respectively.

According to a preferred embodiment, the compositions according to the invention comprise no resin other than the above-described alpha-methylstyrene and, in particular, do not comprise tackifying or sticky resin, in other words resins which contribute a permanent adhesive character to the elastomeric matrix at constant temperature.

In the context of the present invention, the resin is preferably present in a quantity of 5 to 20%, more preferably 5 to 15% by weight, with respect to the total weight of the composition.

In the context of the present invention:
when the content of triblock copolymers is between 5 and 10% by weight, the content of resin is between 15 and 20% by weight, with respect to the total weight of the composition, and
when the content of triblock copolymers is greater than 10% by weight, the content of resin is between 5 and 20% by weight, with respect to the total weight of the composition, and
the percentages being with respect to the total weight of the composition.

In the context of the present invention, the content of triblock copolymers and resin is 16 to 40% by weight, preferably 20 to 35% by weight, with respect to the total weight of the composition.

The Plasticiser

In order to produce interface dressings, the mixture of copolymers and the resin in the composition according to the invention are associated with one (or more) plasticiser compounds.

Suitable plasticisers for use here are well known and intended to improve the stretching, flexibility, extrusion or usage properties of copolymers. If necessary, one or more plasticisers can be used for this purpose.

In general, preferred plasticisers are liquid compounds, compatible with the central saturated olefin block of the above-mentioned block copolymers.

Plasticisers suitable to be used for this purpose include, in particular, plastifying mineral oils.

Alternatively, it is also possible to use synthetic products made from saturated hydrocarbon liquid mixtures such as, for example, the products marketed by TOTAL under the name GEMSEAL® and in particular the product GEMSEAL® 60 which is an isoparaffinic mixture from a fully hydrogenated petroleum fraction.

In the context of the present invention, plasticising oils are preferably used, and in particular mineral oils formed of paraffin or naphthenic compounds, or mixtures thereof, in variable proportions.

Particularly preferred plasticising mineral oils are formed of mixtures of paraffin and naphthenic compounds, and in particular mixtures in which the proportion of paraffin compounds is in the majority.

Particularly suitable plasticising oils include the products marketed by SHELL under the names ONDINA® and in particular ONDINA® 919 or the oil marketed by PETRO CANADA under reference PURETOL® 9D or the oil BLANDOL marketed by Sonneborn, or again the oil Pionier 2076P marketed by Hansen & Rosenthal.

In addition to oils, the plasticiser may also comprise vaseline. The vaseline used in the compositions of the invention is a commercially available vaseline complying with the French Pharmacopoeia.

In the context of the present invention, the vaseline is present in a quantity of 1 to 30%, preferably 5 to 25% by weight, with respect to the total weight of the composition.

In the context of the present invention, the plasticiser is present in a quantity of 50 to 80%, preferably 60 to 70% by weight, with respect to the total weight of the composition.

The plasticiser is preferably composed of a mixture of mineral oil and vaseline, the mineral oil being present in a quantity ranging from 45 to 60% by weight with respect to the total weight of the composition, the vaseline being present in a quantity ranging from 5 to 20% by weight with respect to the total weight of the composition.

On the basis of the test described in the examples of the present application, an elastomeric weave having a breaking force of 1.5 to 2.5 N/cm and an elongation at break of 640% to 900%, preferably 700% to 900% will have improved mechanical properties. In comparison with an identical formulation without resin, the breaking force is improved by at least 40%.

In order to obtain this result, it has been determined that the composition according to the invention preferably comprises:

5 to 20% by weight, of a mixture of two copolymers, comprising at least one copolymer which has a viscosity between 0.01 and 1 Pa·s measured in a 5% mass/mass solution in toluene and at least one copolymer having a viscosity between 0.01 and 0.5 Pa·s measured in a 15% (mass/mass) solution in toluene.

50 to 80% by weight of a mixture of oil and vaseline, 5 to 20% by weight of a resin chosen from the alpha-methylstyrene resins having a softening point in the range between 95 and 105° C. or between 115 and 125° C. or a poly(styrene-co-alpha-methylstyrene) resin having a softening point between 95° C. and 115° C.

The compositions are also used for preparing dressings with or without framework.

The Hydrocolloids

According to a particularly preferred embodiment of the invention in the context of producing interface dressings that are self-supporting, have a substrate or have a framework for the healing of wounds, the compositions according to the invention comprise hydrophilic particles of a hydrocolloid (or hydrocolloid particles).

These particles enable the painless withdrawal of an interface dressing and its retention on the wound in a humid environment, in order to promote healing.

To this effect, a small quantity of hydrophilic particles of a hydrocolloid is thus either deposited on the surface of the elastomeric matrix once this is formed or, preferably, dispersed homogeneously within the composition according to the invention.

Here, "hydrocolloid" or "hydrocolloid particles" shall mean any compound regularly used by a person skilled in the art for its ability to absorb aqueous liquids such as water, physiological serum or the exudates of a wound.

Suitable hydrocolloids include, for example, pectin, alginates, natural plant gums such as, in particular, gum karaya, cellulose derivatives such as carboxymethyl celluloses and their salts of alkali metal salts such as sodium or calcium, as well as synthetic polymers based on acrylic acid salts, known under the name "superabsorbents" such as, for example, the products marketed by CIBA Specialty Chemicals under the name SALCARE® SC91 as well as mixtures of these compounds.

Certain of these superabsorbents, termed "microcolloids" because they have a particle size less than 10 micrometres, can of course also be used.

The preferred hydrocolloids in the context of the present invention are alkali metal salts of carboxymethyl cellulose and, in particular, sodium carboxymethyl cellulose (CMC).

The hydrocolloid particle size is generally between 50 and 100 microns, advantageously of around 80 microns.

In general, the quantity of hydrocolloid particles incorporated in the composition according to the invention is advantageously less than or equal to 25% by weight, advantageously of around 2 to 20% by weight, preferably 5 to 18% by weight, more preferably 10 to 15% by weight, with respect to the total weight of the composition.

If the hydrocolloid particles are deposited at the surface of the elastomeric matrix once this is formed, their quantity will preferably be of around 1 to 10% and more particularly from 2 to 5% by weight, with respect to the total weight of the elastomeric matrix.

The selection of a quantity of hydrocolloid particles within these ranges of values is important for the production of an interface dressing and, in particular, a self-supporting aerated interface dressing, in order to avoid gelling of the composition resulting in closure of the through-holes during the absorption of exudates.

The Antioxidants

The composition according to the invention may also comprise antioxidants.

Here "antioxidants" shall mean compounds commonly used by a person skilled in the art to ensure the stability of compounds in the formulation of compositions, in particular with respect to oxygen, heat, ozone or ultraviolet radiation.

Examples of suitable antioxidants include, in particular, phenolic antioxidants such as, in particular, the products marketed by BASF under the names IRGANOX® 1010, IRGANOX® 565 and IRGANOX® 1076.

In general, these antioxidants can be used alone or in combination in a quantity of around 0.05 to 1% by weight, preferably 0.05 to 0.2% by weight, with respect to the total weight of the composition.

In the context of the present invention, the use of the product IRGANOX® 1010 is preferred in a quantity between 0.05 and 0.2% by weight, with respect to the total weight of the composition.

Additional Active Ingredients

In addition to antioxidants, the composition according to the invention may comprise one or more other active substances for inducing or accelerating healing, or having a favourable role in the treatment of the wound.

These active substances include, in particular, by way of example:

agents promoting healing, such as retinol, vitamin A, vitamin E, N-acetyl hydroxyproline, extracts of Centella asiatica, papain, silicone, essential oils of thyme, niaouli, rosemary and sage, hyaluronic acid, potassium sucrose octasulfate, sucralfate, allantoin and metformin;

antibacterial agents, such as silver salts or complexes (such as silver sulfates, silver nitrates, silver sulfamides or even silver-based zeolites), zinc or copper salts, metronidazole, neomycin, penicillins, clavulanic acid, tetracyclines, minocycline, chlortetracycline, aminoglycosides, amikacin, gentamicin and probiotics;

antiseptics, such as chlorhexidine, trichlosan, biguanide, hexamidine, thymol, lugol's iodine, povidone-iodine, benzalkonium and benzethonium chloride;

painkillers, such as paracetamol, codeine, dextropropoxyphene, tramadol, morphine and its derivatives, corticosteroids and their derivatives;

local anaesthetics, such as lidocaine, benzocaine, dibucaine, pramoxine hydrochloride, bupivacaine, mepivacaine, prilocaine and etidocaine;

anti-inflammatories, such as nonsteroidal anti-inflammatory drugs (NSAIDs), aspirin or acetylsalicylic acid, ibuprofen, ketoprofen, flurbiprofen, diclofenac, aceclophenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid and mefenamic acid.

These active agents can be used in a quantity of around 0.01 to 20% by weight, preferably 1 to 15% by weight, and more preferably 2 to 10% by weight, with respect to the total weight of the composition.

The presence of hydrocolloids within the composition promotes the release of these active agents.

Of course, the composition according to the invention may also comprise one or more other compounds known for their action in the cleaning phase such as, for example:
enzymes;
urea.

Additives

Additives suitable for use in the compositions according to the invention include known compounds for promoting the release of active agents, such as for example the products Montanox® 80 or Sepinov® EMT 10 which are commonly used in URGOTUL® products which incorporate active agents.

These additives can be used in a quantity of around 1 to 15% by weight, with respect to the total weight of the composition.

Clearly, the particular embodiments which have just been described can be implemented separately or according to any of their combinations.

The compositions according to the invention make it possible, in particular, to produce self-supporting interface dressings or interface dressings having a framework or a substrate.

In the context of producing an interface dressing, it is preferable to use a composition which comprises compounds (copolymers, mineral oil, vaseline, antioxidant and hydrocolloids) of the same type as, or identical to, those used in the product URGOTUL®.

Elastomeric Matrix

In order to produce a dressing, the compositions according to the invention are formed as a thin layer, with through-holes, preferably arranged in a distributed manner in said layer in order to form an elastomeric matrix.

The invention also concerns, according to another aspect, an elastomeric matrix obtained from a composition according to the invention such as described above.

The through-holes can be produced by perforating or punching a composition according to the invention, formed beforehand as a thin layer, alone or combined with a temporary substrate or a protective film commonly used for dressing manufacture, or even by a woven coating on a temporary substrate.

Alternatively, the polymer matrices according to the invention can be produced by hot casting of a composition as described above, on a plate etched with the pattern selected for forming the through-holes, followed by cooling and demoulding.

In general, the polymer matrices according to the invention have a thickness between 0.4 mm and 2 mm, preferably between 0.5 mm and 1 mm, more preferably of around 0.6 to 0.7 mm.

The through-holes can be of any geometry and will have, for example, a circular, rectangular, trapezoidal or square cross-section.

The surface area is generally between 1 and 7 mm$^2$.

These holes are preferably distributed in a regular manner, with a density such that the total surface area of the holes is between 20 and 70%, preferably between 30 and 60%, of the total surface area of the dressing.

According to a preferred embodiment, the polymer matrix, when it is used in a preferably self-supporting interface dressing, has the form of an aerated net (or grid), preferably with square mesh, having:
a thickness of the net between 0.4 and 2 mm;
a "thread width" (width of the space between two consecutive holes) between 1 and 10 mm, and preferably between 1 and 5 mm;
a grammage between 200 and 1700 g/m$^2$, and preferably between 300 and 800 g/m$^2$.

According to a particularly preferred embodiment of the invention, such an elastomeric matrix is in the form of an aerated net with square mesh, having:
a thickness of the net of approximately 750 microns;
a thread thickness (or mesh size) of around 0.8 mm;
a grammage of around 390 g/m$^2$.

In order to produce such elastomeric matrices, further details can be found in patent application FR 2 936 158.

It may also be envisaged to use this elastomeric matrix for coating a framework or a substrate.

The techniques for producing an interface dressing with frame or with substrate are also well known to a person skilled in the art and reference can be made, for example, to the methods described in patent applications WO 00 16725 and FR 2 936 159 or WO 2015/018720.

According to a preferred embodiment, the elastomeric matrices obtained by means of compositions according to the invention are not sticky, in other words they have an adhesive power to the skin, determined according to method EN 1939, of less than 40 cN/cm, and preferably less than 35 cN/cm. A substrate sample of width 20 mm and length 150 mm is placed on the forearm. After 10 minutes, the adhesive power is measured using a dynamometer at a traction speed of 900 mm/min with an angle of 90°.

Dressing

The invention also relates, according to a preferred embodiment, to an interface dressing characterised in that it comprises an elastomeric matrix as described above.

According to a currently preferred embodiment, the present application is intended to cover a self-supporting interface dressing comprising an elastomeric matrix in the form of a thin layer possessing through-holes for allowing the passage of exudates, obtained from a composition comprising:
5 to 20% of a mixture of two triblock copolymers of the type styrene-saturated olefin-styrene, a first which has a viscosity between 0.01 and 1 Pa·s as measured in a 5% (mass/mass) solution in toluene and a second which has a viscosity between 0.01 and 0.5 Pa·s as measured in a 15% (mass/mass) solution in toluene,
50 to 80% by weight of at least one plasticiser,
5 to 20% of at least one alpha-methylstyrene resin, having a softening point in the range between 80 and 125° C., preferably between 90 and 110° C.,
it being understood that:
when the content of triblock copolymers is between 5 and 10% by weight, the content of resin is between 15 and 20% by weight, with respect to the total weight of the composition, and when the content of triblock copolymers is greater than 10% by weight, the content of resin is between 5 and 20% by weight, with respect to the total weight of the composition, and the percentages being with respect to the total weight of the composition.

Preferably, the interface dressing according to the invention does not adhere to latex gloves. To achieve this, the composition may preferably comprise:

for 100 parts by weight of a mixture P of two specific triblock copolymers of the type styrene-saturated olefin-styrene, a first which has a viscosity between 0.01 and 1 Pa·s as measured in a 5% (mass/mass) solution in toluene and a second which has a viscosity between 0.01 and 0.5 Pa·s as measured in a 15% (mass/mass) solution in toluene;

300 to 1000 parts by weight of a plasticiser H, preferably an oil plasticiser; and 90 to 600 parts by weight of vaseline V;

it being also specified that:

the total quantity, represented by P+H+V, of mixture of elastomers, plasticiser and vaseline is between 490 and 1700 parts by weight;

the ratio between the total quantity of the mixture of elastomer, plasticiser and vaseline and the quantity of vaseline, represented by P+H+V/V, is less than 11;

said mixture of two copolymers comprises at least 20% by weight of the first copolymer, the composition also comprising 5 to 20% by weight of an alpha-methylstyrene resin, having a softening point between 80 and 125° C., preferably between 90 and 110° C.

it being understood that:

when the content of triblock copolymers is between 5 and 10% by weight, the content of resin is between 15 and 20% by weight, with respect to the total weight of the composition, and when the content of triblock copolymers is greater than 10% by weight, the content of resin is between 5 and 20% by weight, with respect to the total weight of the composition, and the percentages being with respect to the total weight of the composition.

In order to protect the composition from the external environment, the interface dressing can be covered, preferably on each of its faces, by a temporary protective film which will be removed before use by the user.

In order to further facilitate the handling of the interface dressing, in particular if it is self-supporting, the two temporary protective films can be substituted by a single protection such as described in patent application WO2008/145884 or in patent application WO2015/018720, the structure of which particularly facilitates the application of the dressing on the wound.

The present invention is illustrated in the non-limiting examples presented below.

EXAMPLES

Preparation of the Compositions

The compositions of examples 1 to 26 have been developed using the following constituents in the proportions, expressed in percentage by weight, listed in table 1 below.

Elastomer: block copolymer with poly(styrene-ethylene-butylene-styrene) (abbreviated as SEBS):

KRATON® G 1654 ES viscosity at 5% (mass/mass) in toluene: 0.02 Pa·s

KRATON® G 1650 E viscosity at 15% (mass/mass) in toluene: 0.2 Pa·s

Plasticiser: mineral oil Ondina® 919 marketed by SHELL or Pionier 2076P marketed by Hansen & Rosenthal Vaseline: vaseline Codex® A marketed by AIGLON Antioxidant: IRGANOX® 1010 marketed by BASF Hydrocolloid: Sodium carboxymethyl cellulose CMC BLANOSE® 7H4XF marketed by ASHLAND, Resins:

Wingtack 86, C9 modified C5 hydrocarbon resin, having a softening point in the range between 84-90° C., marketed by Cray Valley, Norsolene W90 or Cleartack W90, poly(styrene-co-alpha-methylstyrene) resin having a softening point in the range between 85-95° C., marketed by Cray Valley, Norsolene W140, poly(styrene-co-alpha-methylstyrene) resin having a softening point in the range between 135-145° C., marketed by Cray Valley, Escorez 5380, cycloaliphatic hydrocarbon resin, having a softening point in the range between 80-90° C., marketed by Exxon Mobil, YS Resin SX 100, polystyrene resin, having a softening point at 100° C., marketed by YASUHARA CHEMICAL, Sylvares SA 100, alpha-methylstyrene resin having a softening point in the range between 95 and 105° C., marketed by Arizona Chemical/Kraton Polymer Sylvares SA 120, alpha-methylstyrene having a softening point in the range between 115 and 125° C., marketed by Arizona Chemical/Kraton Polymer Kristalex 3100LV, poly(styrene-co-alpha-methylstyrene) resin having a softening point at 100° C., marketed by Eastman, Kristalex F100 poly(styrene-co-alpha-methylstyrene) having a softening point in the range between 96 et 104° C., marketed by Eastman, Kristalex F115, poly(styrene-co-alpha-methylstyrene) resin having a softening point in the range between 114 and 120° C., marketed by Eastman, Kristalex 5140, poly(styrene-co-alpha-methylstyrene) resin having a softening point of 139° C., marketed by Eastman, Sukorez SU-400, polycyclopentadiene resin having a softening point in the range between 97 and 107° C., marketed by Kolon Industries.

Production of the Composition

The plasticiser, the hydrocolloid and the vaseline were successively introduced into a vertical mixer at a setpoint temperature of 90° C. and stirred until a homogeneous mixture was obtained.

The copolymer or copolymers, antioxidant and resin or resins were then introduced under stirring, then the temperature was taken to a setpoint at 150° C. and stirred until a homogeneous mixture was obtained. The mixer was then placed under vacuum in order to remove the bubbles present in the mixture.

Following this, the mixer was left to cool and then drained.

Next, polymer matrices were produced from the compositions to be tested, by applying a high pressure by means of a hydraulic press, according to the following protocol:

The two plates of the hydraulic press were preheated. A non-stick plastic film was deposited on the lower plate of the press, for example a siliconised-fluorinated polyester film (the siliconised-fluorinated face being arranged opposite the lower plate). Approximately 12 g of one of the described compositions was deposited on the face and covered by a siliconised polyester film (the siliconised side being arranged in contact with the composition). Two 0.75 mm shims were placed between the two polyester films at the ends of the lower plate of the press and the assembly was subjected to a pressure of 200 bars and a temperature of around 90 to 100° C.

The plates produced in this way were left to cool and their thickness was checked using a micrometre so as to obtain a model with thickness of around 650 µm.

Measurement of the Breaking Force and Elongation at Break:

The conditions for carrying out the test and the models used were as follows.

The principle of this measurement is to exert a tensile force on a dumbbell test piece (corresponding to a die-cut elastomeric weave) at constant speed V until breaking, using a dynamometer.

Hence, the force at breaking and elongation at break are measured.

Materials and Apparatus
Automatic press+thickness shims,
Electronic dynamometer (0.1 to 999 mm/min),
Force sensor (to be adjusted to the force to be measured),
Die-cut dumbbell test piece,
Material type, mechanical polyurethane foam 400 µm Exopack.
Sampling/Sample Conditioning
Number of test pieces, n≥5.
Conditioning time T>24 h.
Temperature T=23° C.±2° C.
Hygrometry RH=50%±15%.

Operating Conditions:
l (width of test piece)=12.7 mm
$l_0$ (distance between the jaws of the dynamometer)=90 mm
V (traction speed)=300 mm/min
Procedure
Preparation of the Test Pieces:
degas the composition to be analysed, beforehand,
using the automatic press, prepare elastomeric matrix plates with thickness 650 µm from the degassed composition (750 µm shims),
cut-out the dumbbell test pieces using the cutting die, being careful not to start.
Measurement
Place a dumbbell test piece of width 12.7 mm in the jaws of the dynamometer spaced at $l_0$=90 mm, covering the two ends beforehand with mechanical PU foam 400 µm (in order to avoid shearing of the test piece in the jaws),
continue the tensile test until breaking of the test piece, at speed V=300 mm/min,
check that the break front is produced in the straight portion of the test piece.
Calculations/Expression of the Results
Extract the force values at breaking and associated elongation at breaking from the curve.
Calculate, for each sample reference:
the minimum,
the maximum,
the mean,
the standard deviation, and
the CV.

TABLE 1

|  | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Ex. 13 |
|---|---|---|---|---|---|---|---|---|---|---|---|---|---|
| Kraton G1654 ES | 5.7 | 5.7 | 5.7 | 5.7 | 5.7 | 5.7 | 5.7 | 5.7 | 5.7 | 5.7 | 5.7 | 5.7 | 5.7 |
| Kraton G 1650E | 2.6 | 2.6 | 2.6 | 2.6 | 2.6 | 2.6 | 2.6 | 2.6 | 2.6 | 2.6 | 2.6 | 2.6 | 2.6 |
| Ondina 919 | 61.5 | 57.5 | 53.5 | 46.9 | 53.5 | 57.5 | 53.5 | 53.5 | 53.5 | 53.5 | 53.5 | 57.5 | 57.5 |
| Pionier 2076P |  |  |  |  |  |  |  |  |  |  |  |  |  |
| Vaseline Codex A | 15 | 14 | 13 | 11.4 | 13 | 14 | 13 | 13 | 13 | 13 | 13 | 14 | 14 |
| CMC Blanose | 15 | 15 | 15 | 13.2 | 15 | 15 | 15 | 15 | 15 | 15 | 15 | 15 | 15 |
| Irganox 1010 | 0.2 | 0.2 | 0.2 | 0.2 | 0.2 | 0.2 | 0.2 | 0.2 | 0.2 | 0.2 | 0.2 | 0.2 | 0.2 |
| Norsolene W90 |  | 5 | 10 | 20 |  |  |  |  |  |  |  |  |  |
| Escorez 5380 |  |  |  |  | 5 |  |  |  |  |  |  |  |  |
| YS Resin |  |  |  |  | 5 | 5 | 10 |  |  |  |  |  |  |
| Sylva res SA 100 |  |  |  |  |  |  |  | 10 |  |  |  |  |  |
| Kristalex F115 |  |  |  |  |  |  |  |  | 10 |  |  |  |  |
| Sylvares SA 120 |  |  |  |  |  |  |  |  |  | 10 |  |  |  |
| Kristalex 5140 |  |  |  |  |  |  |  |  |  |  | 10 | 5 |  |
| Norsolène W140 |  |  |  |  |  |  |  |  |  |  |  |  | 5 |
| Wingtack 86 |  |  |  |  |  |  |  |  |  |  |  |  |  |
| Kristalex 3100LV |  |  |  |  |  |  |  |  |  |  |  |  |  |
| Kristalex F100 |  |  |  |  |  |  |  |  |  |  |  |  |  |
| Sukorez SU 400 |  |  |  |  |  |  |  |  |  |  |  |  |  |
| Force rupture (N/cm) | 0.76 | 0.94 | 1.23 | 2.3 | 1.04 | 0.96 | 1.37 | 1.43 | 1.36 | 1.38 | 1.13 | 0.86 | 0.96 |
| Allongement (%) | 283 | 450 | 565 | 741 | 443 | 390 | 469 | 538 | 500 | 487 | 332 | 323 | 395 |

|  | Ex. 14 | Ex. 15 | Ex. 16 | Ex. 17 | Ex. 18 | Ex. 19 | Ex. 20 | Ex. 21 | Ex. 22 | Ex. 23 | Ex. 24 | Ex. 25 | Ex. 26 | Ex. 27 |
|---|---|---|---|---|---|---|---|---|---|---|---|---|---|---|
| Kraton G1654 ES | 5.7 | 7.8 | 7.8 | 7.8 | 7.8 | 7.8 | 7.8 | 7.8 | 7.8 | 11.3 |  | 7.8 | 7.8 | 7.8 |
| Kraton G 1650E | 2.6 | 3.5 | 3.5 | 3.5 | 3.5 | 3.5 | 3.5 | 3.5 | 3.5 |  | 11.3 | 3.5 | 3.5 | 3.5 |
| Ondina 919 | 53.5 | 61.5 | 57.5 | 53.5 | 53.5 |  |  |  |  |  |  |  |  |  |
| Pionier 2076P |  |  |  |  |  | 53.5 | 53.5 | 53.5 | 53.5 | 53.5 | 53.5 | 53.5 | 53.5 | 53.5 |
| Vaseline Codex A | 13 | 12 | 12 | 12 | 12 | 12 | 12 | 12 | 12 | 12 | 12 | 12 | 12 | 12 |
| CMC Blanose | 15 | 15 | 15 | 13 | 13 | 13 | 13 | 13 | 13 | 13 | 13 | 13 | 13 | 13 |
| Irganox 1010 | 0.2 | 0.2 | 0.2 | 0.2 | 0.2 | 0.2 | 0.2 | 0.2 | 0.2 | 0.2 | 0.2 | 0.2 | 0.2 | 0.2 |
| Norsolene W90 |  |  | 5 | 10 |  |  | 10 |  |  |  |  |  |  |  |
| Escorez 5380 |  |  |  |  |  |  |  |  |  |  |  |  |  |  |
| YS Resin |  |  |  |  |  |  |  |  |  |  |  |  |  |  |

TABLE 1-continued

| | | | | | | | | | | | | | | |
|---|---|---|---|---|---|---|---|---|---|---|---|---|---|---|
| Sylva res SA 100 | | | | | 10 | | 10 | | | | | | | |
| Kristalex F115 | | | | | | | | | | | | | | 10 |
| Sylva res SA 120 | | | | | | | | | | | | | | |
| Kristalex 5140 | | | | | | | | | | | | | | |
| Norsolène W140 | 10 | | | | | | | | | | | | | |
| Wingtack 86 | | | | | | 10 | | | | | | | | |
| Kristalex 3100LV | | | | | | | | 10 | 10 | 10 | | | | |
| Kristalex F100 | | | | | | | | | | | | 10 | | |
| Sukorez SU 400 | | | | | | | | | | | | | 10 | |
| Force rupture (N/cm) | 1.36 | 1.31 | 1.62 | 2.24 | 2.2 | 1.26 | 1.87 | 2.19 | 2.15 | 3.43 | 0.77 | 2 | 1.29 | 2.42 |
| Allongement (%) | 487 | 511 | 642 | 785 | 754 | 558 | 792 | 826 | 864 | 1156 | 228 | 849 | 665 | 806 |

The matrix obtained in examples 1 and 15, which does not contain resin, exhibits poor results for the breaking force and elongation at breaking.

The matrix obtained in examples 2 and 3 (and those of examples 5 to 14) have a total triblock copolymer content less than 10% by weight and a resin content less than 15%, which does not allow good results for breaking force and elongation at breaking to be obtained. By contrast, the matrix obtained in example 4 according to the invention, having a total triblock copolymer content less than 10% by weight and resin content of 20%, exhibits good results for breaking force and elongation at breaking, which is manifested by good mechanical properties, in particular the tear strength.

Moreover, the elastomeric matrices obtained in examples 5, 6, 7, 11, 12, 13 and 14 using resins which are not according to the present invention, do not give good breaking force and elongation of breaking results.

The elastomeric matrices obtained in examples 5, 6, 7, 11 and 12 also exhibit a whitish colour, characteristic of an instability of the mixture and deceptive from an aesthetic point of view.

The elastomeric matrices obtained in examples 16, 17, 18, 20, 21, 22, 25 and 27 in accordance with the invention have good results for breaking force and elongation at breaking, which is manifest as good mechanical properties, in particular tear strength.

The elastomeric matrix obtained in examples 19 and 26, using resins which are not according to the present invention, does not give good breaking force and elongation of breaking results.

The elastomeric matrices of examples 23 and 24, containing only a single triblock column according to the invention, are also not satisfactory in terms of tear strength.

The invention claimed is:

1. A self-supporting elastomeric matrix without framework comprising:
   5 to 20% of a mixture of two triblock copolymers of a type styrene-saturated olefin-styrene, a first which has a viscosity between 0.01 and 1 Pa·s as measured in a 5% (mass/mass) solution in toluene and a second which has a viscosity between 0.01 and 0.5 Pa·s as measured in a 15% (mass/mass) solution in toluene,
   50 to 80% by weight of at least one plasticiser,
   5 to 20% of at least one alpha-methylstyrene resin having a softening point in a range between 95 and 110° C. or a poly(styrene-co-alpha-methylstyrene) resin having a softening point between 95° C. and 115° C.,
   wherein:
      when the content of triblock copolymers is between 5 and 10% by weight, a content of resin is between 15 and 20% by weight, with respect to the total weight of the matrix, and
      when the content of triblock copolymers is greater than 10% by weight, a content of resin is between 5 and 20% by weight, with respect to the total weight of the matrix, and the percentages being with respect to the total weight of the matrix.

2. The self-supporting elastomeric matrix without framework according to claim 1, wherein the resin is chosen from an alpha-methylstyrene resin having a softening point in a range between 95 and 105° C.

3. The self-supporting elastomeric matrix without framework according to claim 1, wherein the plasticiser is composed of a mixture of mineral oil and vaseline.

4. The self-supporting elastomeric matrix without framework according to claim 1, wherein it comprises hydrocolloid particles in a quantity less than or equal to 25% by weight, with respect to the total weight of the composition matrix.

5. The self-supporting elastomeric matrix without framework composition according to claim 1, wherein it comprises one or more active substances for inducing or accelerating healing or able to play a beneficial role in the treatment of wounds, in a quantity between 0.01 and 20% by weight, with respect to the total weight of the matrix.

6. The self-supporting elastomeric matrix without framework according to claim 1, obtained by formation of a thin layer and compression, or by hot casting of the matrix.

7. The self-supporting elastomeric matrix without framework according to claim 1, comprising through-holes.

8. The self-supporting elastomeric matrix without framework according to claim 1, wherein it is in the shape of an aerated net with a mesh size of around 4 mm$^2$, thickness of around 800 microns and grammage of around 400 g/m$^2$.

9. An interface dressing, wherein it comprises the elastomeric matrix without framework according to claim 1.

10. The self-supporting elastomeric matrix without framework according to claim 1, wherein it comprises one or more active substances for inducing or accelerating healing or able to play a beneficial role in the treatment of wounds, in a quantity between 1 and 15% by weight, with respect to the total weight of the matrix.

11. The self-supporting elastomeric matrix without framework according to claim 1, wherein the saturated olefins are chosen from ethylene-butylene, ethylene-propylene or ethylene-ethylene-propylene blocks.

* * * * *